US00PP30150P3

(12) United States Plant Patent
Jordan

(10) Patent No.: US PP30,150 P3
(45) Date of Patent: Jan. 29, 2019

(54) ARTICHOKE PLANT NAMED 'SJ 857'

(50) Latin Name: *Cynara scolymus*
Varietal Denomination: SJ 857

(71) Applicant: Steve Jordan, Lompoc, CA (US)

(72) Inventor: Steve Jordan, Lompoc, CA (US)

(73) Assignee: BARODA FARMS, INC., Lompoc, CA (US)

( * ) Notice: Subject to any disclaimer, the term of this patent is extended or adjusted under 35 U.S.C. 154(b) by 0 days.

(21) Appl. No.: 15/530,949

(22) Filed: Mar. 27, 2017

(65) Prior Publication Data

US 2017/0290226 P1 Oct. 5, 2017

Related U.S. Application Data

(60) Provisional application No. 62/390,546, filed on Apr. 1, 2016.

(51) Int. Cl.
*A01H 5/02* (2018.01)

(52) U.S. Cl.
USPC ..... Plt./258
CPC ..... *A01H 5/02* (2013.01)

(58) Field of Classification Search
USPC ..... Plt./258
CPC ... A01H 5/06; A01H 5/12; A01H 5/02; A01H 5/08; A01H 5/00; A01H 6/14
See application file for complete search history.

(56) References Cited

U.S. PATENT DOCUMENTS

PP17,283 P2 * 12/2006 Jordan ..... A01H 5/025 Plt./258
PP21,688 P2 * 2/2011 Jordan ..... A01H 5/025 Plt./258

* cited by examiner

*Primary Examiner* — June Hwu
(74) *Attorney, Agent, or Firm* — Ballew Law

(57) ABSTRACT

A new and distinct cultivar of *Cynara scolymus* named 'SJ 857' distinguishable from all other *Cynara scolymus,* by productive yield, and yellow-green immature flower buds that are very large in size and spherical in shape. In combination these traits set 'SJ 857' apart from all other existing varieties of *Cynara scolymus* known to the inventor.

5 Drawing Sheets

Genus and species: *CYNARA scolymus.*
Variety denomination: 'SJ 857'.

STATEMENT REGARDING FEDERALLY SPONSORED RESEARCH OR DEVELOPMENT

None

BACKGROUND AND SUMMARY OF THE VARIETY

The present invention relates to a new and distinct cultivar of globe artichoke plant, a perennial herb that is grown as a food crop for the production of edible vegetable delicacies. The new invention is known botanically as *CYNARA scolymus* and will be referred to hereinafter by the cultivar name 'SJ 857'. *Cynara* is in the family Asteraceae, formerly known as Compositae.

An individual plant of *Cynara scolymus* 'SJ 857' is comprised of main stem, lateral stems, leaves, and immature flower buds known as involucre. Each involucrum is made up of phyllaries also known as involucral bracts. The edible parts of freshly harvested immature flower buds are the fleshy part of the bracts, the fleshy receptacle, and the uppermost part of the peduncle. If not harvested, but permitted to mature, flower buds will develop into flower heads known as capitula.

In 2011 the inventor collected seed from the mature inflorescence of an individual *Cynara scolymus* 'Z530' (U.S.

Plant Pat. No. 21,688 P2) plant that was grown in a cage in Maricopa, Calif. with other 'Z530' plants. Maricopa is in Kern County. Prevailing winds typically blow from west to east. In April the average temperature is 24.40° Celsius. Annual rainfall is 15.24 cm. and the soil is alluvial loam.

Said seed was sown by the inventor in Lompoc, Calif. in 2012 with the intention of making selections from the resulting crop. Lompoc is located on California's central coast in Santa Barbara County. Conditions vary with air temperatures ranging from 15.5° Celsius to 26.6° Celsius. The relative humidity is generally high. Prevailing winds are northwesterly and rainfall averages 30.48 cm. per year.

From resulting progeny, the inventor made selections based on criteria of immature flower bud size and productive yield From said selections the inventor discovered 'SJ 857' in 2013. The inventor selected 'SJ 857' in 2013 based on criteria of productive yield and green immature flower buds that are very large in size. Increases were made at this time by vegetative cuttings. In 2014 'SJ 857' continued to show high productive yield of large, spherical immature flower buds, and the vegetative cuttings then served as explant material for subsequent asexual propagation by tissue culture in 2014. Tissue culture was initiated by meristemming followed by shoot multiplication, rooting, and acclimatization.

The new cultivar 'SJ 857' is a seedling variant derived from the parent (male and female parent), an individual *CYNARA scolymus* 'Z530' (U.S. Plant Pat. No. 21,688 P2). Compared to 'Z530', the new cultivar is different because the involucrum shape is spherical, while 'Z530' has an oblate involucrum shape. 'SJ 857' has 130 inner bracts per involucrum and 'Z530' has 50 inner bracts per involucrum. Additionally, the involucrum size of 'SJ 857' is double the number of large involucrums per plant. The involucrum size of the parent plant 'Z530' has a similar involucrum yield but smaller involucrums.

The closest comparison plant is *Cynara scolymus* 'X42' (U.S. Plant Pat. No. 21,699 P2). The new cultivar 'SJ 857' is distinguishable from the comparison plant by immature flower bud shape, and immature flower bud size. The new cultivar 'SJ 857' has twice as many large sized artichokes as the comparison plant.

From 2014 to 2017 the inventor increased numbers of 'SJ 857' to four thousand plants through both vegetative cuttings and tissue culture. Vegetative cuttings were done outdoors in Lompoc, Calif. while tissue culture was completed in a tissue culture lab in Lompoc, Calif. The new cultivar 'SJ 857' is determined uniform, stable, and true to type in subsequent generations of vegetative propagation. Cultural requirements include full sun, well-draining alluvial soil, and moderate water. Hardiness is classified as USDA Zone 6.

SUMMARY OF THE INVENTION

The following traits have been repeatedly observed and represent the distinguishing characteristics of the new cultivar named 'SJ 857'. These traits in combination distinguish 'SJ 857' from all other existing cultivars of *Cynara sclyymus* known to the inventor. 'SJ 857' has not yet been tested under all possible conditions and phenotypic differences may be observed with variations in environmental, climatic, and cultural conditions, however, without any variance in genotype.

1. 'SJ 857' exhibits productive yield;
2. 'SJ 857' exhibits immature flower buds that are very large in size, with twice as many large artichokes as 'X42' (U.S. Plant Pat. No. 21,699 P2), its comparison plant;
3. 'SJ 857' exhibits immature flower buds that are light yellow-green in color;
4. 'SJ 857' exhibits immature flower buds that are spherical in shape;
5. 'SJ 857' is asexually reproduced using vegetative cuttings and tissue culture;
6. 'SJ 857' is asexually reproduced using vegetative cuttings and tissue culture; and
7. 'SJ 857' is classified as USDA Zone 6.

BRIEF DESCRIPTION OF THE DRAWINGS

The accompanying color drawings illustrate the overall appearance of the new and distinct cultivar named 'SJ 857' showing color as true as is reasonably possible to obtain in color reproductions of this type. Color in the drawings may differ from color values cited in the detailed botanical description, which accurately describe the actual color of the new variety 'SJ 857'. The drawings were made using conventional techniques and although immature flower bud and foliage color may appear different from actual color due to light reflectance, it is as accurate as possible by conventional photography.

DETAILED BOTANICAL DESCRIPTION

Figure 1:
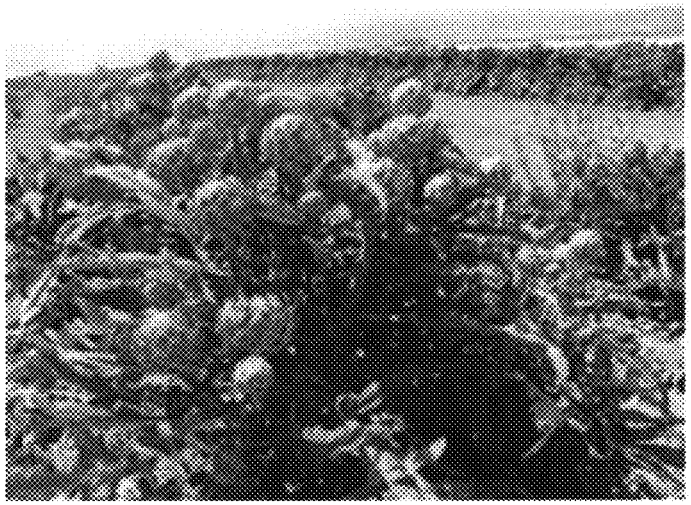
FIG. 1 depicts a whole plant of 'SJ 857'.
Figure 2:
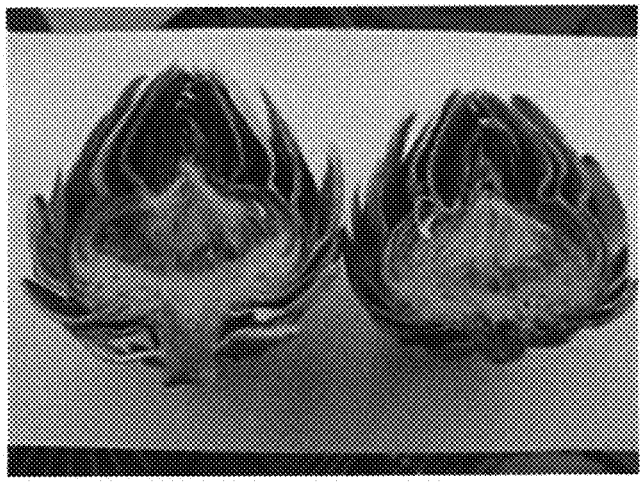
FIG. 2 depicts two mature heads of 'SJ 857' cut in half.
Figure 3:
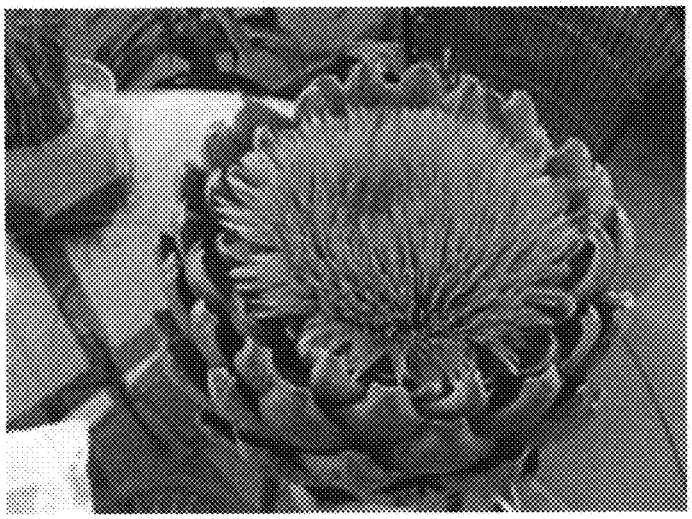
FIG. 3 depicts a mature flower of 'SJ 857'.
Figure 4:
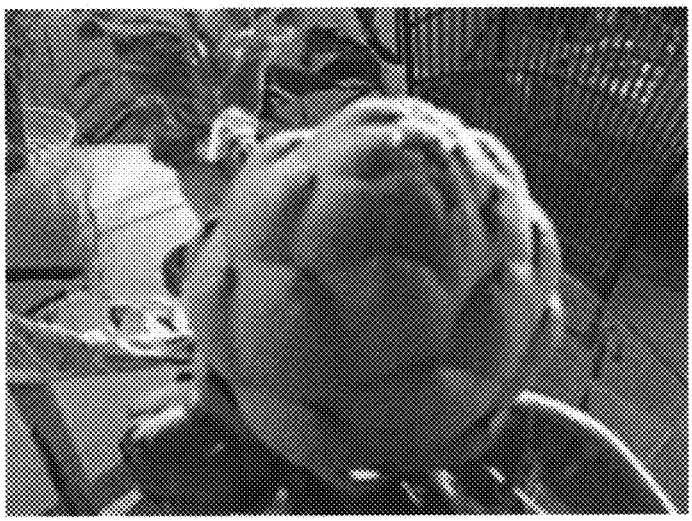
FIG. 4 depicts an immature flower bud of 'SJ 857'.
Figure 5:
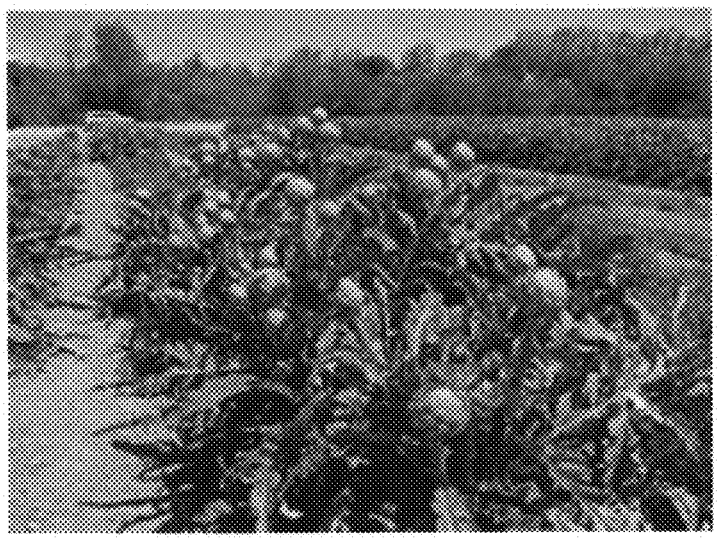
FIG. 5 depicts a row of 'SJ 857' plants.

The following is a detailed botanical description of 'SJ 857' as grown in California under conditions typically used in agricultural practices. Color determinations are in accordance with The 2001 Royal Horticultural Society Colour Chart of London, England, except where general color terms of ordinary dictionary significance are used. The following observations, measurements and values were collected from plants grown in Lompoc, Calif. and plants grown in Maricopa, Calif. Data was collected in April and May of 2017, from plants grown in rows where row spacing (bed centers) was 2 meters and individual plant spacing was 1.22 meters. Growing requirements are similar to the species. No chemicals known to the inventor were used to induce plant growth.

Botanical classification: *CYNARA scolymus* 'SJ 857'.
Family: Asteraceae (formerly Compositae).
Genus: *CYNARA*.
Species: *scolymus*.
Denomination: 'SJ 857'.
Common name: Globe artichoke.
Commercial classification: Fresh market food crop.
Months of harvest: Year round with greatest productivity March through October.
Lompoc crop age: 2-years-old.
Maricopa crop age: 7 months.
Use: Production of edible vegetable delicacies.
Parentage: *Cynara scolymus* 'SJ 857' discovered by inventor as a seedling variant derived from the following parent:
*Parent*.—An individual *CYNARA scolymus* 'Z530' (U.S. Plant Pat. No. 21,688 P2).
Plant description:
*Habit*.—Upright.
*Vigor*.—Vigorous.
*Type*.—Perennial herb.
*Height* (*average*).—122 cm.
*Width* (*average*).—198 cm.
*Root system*.—Thick and fibrous.
*Hardiness*.—USDA Zone 6.
*Propagation method*.—Tissue culture and vegetative cuttings.
*Field crop time* (*average*).—5-6 months to produce a harvestable crop of edible immature flower buds.
*Disease resistance*.—None known to the inventor.
*Pest and disease susceptibility*.—Aphids, slugs, and leaf spot.
*Cultural requirements*.—Grow in full sun and well-draining alluvial soil, with moderate water.
*Stem*.—Branching habit (range): Basal to cauline. Stem density: Dense. Main stem diameter (average): 5 cm. Main stem height (average): 35 cm. Main stem surface Ribbed. Main stem shape: Cylindric. Main stem quantity (average): 1 per plant. Lateral stem quantity (average): 3 per plant. Lateral stem diameter (average): 3.75 cm. Lateral stem length (range) 27.50 cm. to 60 cm. Stem strength: Rigid. Stem color: 148B. Internode (range): 6 cm. to 9 cm.
*Foliage*.—Type: Evergreen. Arrangement: Alternate. Shape: Lanceolate. Division: Simple. Margin (range): Entire to pinnately lobed. Quantity (average): 112 leaves per plant. Attachment: Decurrent. Abaxial surface leaf color: 137D. Adaxial surface leaf color 137C. Leaf length (average): 115 cm. Leaf width (average): 70 cm. Leaf apex(range): Acute to narrow acute. Leaf base: Truncate. Lobe quantity (average): 15 per leaf. Lobe apex: Rounded. Lobe length (range): 3 cm.-21 cm. Lobe width (range): 3 cm.-7 cm. Venation pattern: Reticulate. Vein color (abaxial surface): 145A. Vein color (adaxial surface): 145A. Leaf surface (abaxial surface): Tomentose. Leaf surface (adaxial surface): Puberulent. Appearance (abaxial surface): Matte. Appearance (adaxial surface): Matte. Stipules: None observed. Fragrance None observed. Spines: None observed. Angle of leaf to stem (average): 45°.

*Involucrum* (*immature flower bud*).—Shape: Spherical. Apex: Rounded. Base: Rounded. Diameter (average): 15.0 cm. Height (average): 15.0 cm. Form: Compact. Texture: Firm. Surface Glabrous. Quantity (average): 17 per plant. Immature flower bud color: 148C. Immature flower bud striation color: 157A. Phyllary (involucral bract): Arrangement: Imbricate. Outer bract quantity (average): 45 per involucrum. Inner bract quantity (average): 130 per involucrum. Outer bract shape: Ovate. Inner bract shape: Oblong. Outer bract apex (range): Acute to retuse. Outer bract base: Truncate. Inner bract apex. Acute. Inner bract base: Truncate. Outer bract margin: Entire. Inner bract margin: Entire. Outer bract texture: Sarcous. Inner bract texture: Sarcous. Bract dimensions: Outer bract height (average): 7 cm. Outer bract width (average): 5.50 cm. Inner bract height (average): 7.25 cm. Inner bract width (average); 4.50 cm. Outer bract base (average) 3 cm. Inner bract base (average): 2 cm. Outer bract surface: Glabrous. Inner bract surface Glabrous. Outer bract color: 148C. Outer bract marking: Striations. Outer bract striation color: 157A. Inner bract color (range): 145D to 146D. Inner bract markings color (range): N186A to N186D. Outer bract appearance: Matte. Inner bract appearance: Argenteous. Spines (inner & outer bracts): Spinescent. Spine length (average): 1 mm. Spine color: 165D. Receptacle shape: Concavo-concave. Receptacle diameter (average) 8 cm. Receptacle height (average): 2 cm. Receptacle color: 158D. Receptacle texture: Firm. Pappus height (average): 2.50 cm. Pappus diameter (average): 6 cm. Pappus color (range): 158D. Bristle quantity: >500. Bristle shape: Filament. Bristle color: 158D. Bristle height (average): 3 cm. Bristle width (average): <0.50 mm. Bristle texture: Sericeous. Peduncle shape: Cylindric. Peduncle length (range) 27.50 cm. to 60 cm. Peduncle diameier (average): 3.75 cm. Peduncle color: 148B. Peduncle strength: Rigid. Peduncle surface: Ribbed. Duration of cold storage (range): 22-24 days. Cold storage temperature (range): 1° to 2° Celsius. Cold storage response: Negligible browning of outer bracts and stem cut. Shelf life (range): 22-28 days under mist. Weight (average): 779.8 grams.

*Mature inflorescence*.—Type: Capitula. Persistent or self-cleaning: Persistent. Fragrance: Mild fruity scent. Shape: Oblate. Weight (average): 907 grams. Appearance: Thistle-like. Height (average): 16 cm. Diameter (average): 19 cm. Spines: Armed. Bract: Arrangement: Imbricate. Outer bract quantity (average): 50 per inflorescence. Inner bract quantity (average): >100 per inflorescence. Outer bract shape: Deltoid. Outer bract form: Involute. Inner bract shape: Oblong. Margin (outer and inner bract): Entire. Outer bract texture: Coriaceous. Inner bract texture: Papyraceous. Outer bract height (average): 9 cm. Outer bract width (average): 6 cm. Inner bract height (average): 7 cm. Inner bract width (average): 1 cm. Outer bract surface (ventral and dorsal): Glabrous. Inner bract surface (ventral and dorsal): Glabrous. Outer bract color (ventral and dorsal surface): 148D. Outer bract shading (dorsal surface): N77C. Inner bract color dorsal surface (range): 165A to 165D. Inner bract color ventral surface: N155D. Outer bract appearance: Matte. Inner bract appearance. Argenteous. Outer bract apex: Narrow acute. Outer bract apex form: Interior ring reflexed. Outer bract base: Truncate. Outer bract base width (average): 3.50 cm. Inner bract apex: Narrow acute. Inner bract base: Truncate. Inner bract base width (average): 0.75 cm. Receptacle shape: Concavo-concave. Receptacle diameter (average): 10 cm. Receptacle depth (average): 2.50 cm. Receptacle texture: Firm. Receptacle color: 159C. Disc floret quantity (average): >500. Corolla dimensions: 1.20 cm in height and <3 mm. in diameter. Corolla tube color: N77C. Pappus appearance: Argenteous. Pappus texture: Sericeous. Pappus color: 165D. Bristle quantity (average): >500 per capitula. Bristle shape: Filamentous. Bristle color: 165D. Bristle length (average): 6 cm. Bristle texture: Sericeous. Peduncle shape: Cylindric. Peduncle diameter (average): 2 cm. Peduncle length (average): 35 cm. Peduncle color: 148B. Peduncle strength: Rigid. Peduncle surface: Ribbed.

*Reproductive organs*.—Style color: 86B. Style dimensions: 5.50 cm. in height and <1 mm. in diameter. Stamen: Epipetalous. Anther: Connate. Filament: Adnate to corolla. Ovary: Ovate. Ovary dimensions: 5 mm in height and 5 mm. in width. Ovary color: 165D. Ovary position: Inferior.

*Seed*.—None observed.

The invention claimed is:

1. A new and distinct cultivar of *Cynara scolymus* plant named 'SJ 857' as shown, described and illustrated herein.

* * * * *